United States Patent
Cho et al.

(10) Patent No.: US 8,705,033 B2
(45) Date of Patent: *Apr. 22, 2014

(54) MULTI-CHANNEL SURFACE PLASMON RESONANCE SENSOR USING BEAM PROFILE ELLIPSOMETRY

(75) Inventors: Hyun Mo Cho, Daejeon (KR); Yong Jai Cho, Daejeon (KR); Won Chegal, Daejeon (KR)

(73) Assignee: Korea Research Institute of Standards and Science (KR)

( * ) Notice: Subject to any disclaimer, the term of this patent is extended or adjusted under 35 U.S.C. 154(b) by 247 days.

This patent is subject to a terminal disclaimer.

(21) Appl. No.: 13/128,090

(22) PCT Filed: Nov. 30, 2009

(86) PCT No.: PCT/KR2009/007083
§ 371 (c)(1),
(2), (4) Date: May 6, 2011

(87) PCT Pub. No.: WO2010/062149
PCT Pub. Date: Jun. 3, 2010

(65) Prior Publication Data
US 2011/0216320 A1    Sep. 8, 2011

(30) Foreign Application Priority Data
Nov. 28, 2008    (KR) .................. 10-2008-0120134

(51) Int. Cl.
*G01J 4/00*    (2006.01)
*G01N 21/55*    (2006.01)
(52) U.S. Cl.
USPC .......................................... 356/369; 356/445

(58) Field of Classification Search
None
See application file for complete search history.

(56) References Cited

U.S. PATENT DOCUMENTS

| 8,149,411 B2 * | 4/2012 | Johansen et al. ............... 356/445 |
| 2006/0221343 A1 | 10/2006 | Bouhelier et al. |
| 2008/0032326 A1 | 2/2008 | Greenbaum et al. |
| 2010/0045985 A1 | 2/2010 | Lee et al. |
| 2012/0057416 A1 * | 3/2012 | Zampaglione et al. .. 365/189.09 |

FOREIGN PATENT DOCUMENTS

| KR | 10-2007-0039335 | 4/2007 |
| KR | 100742982 | 7/2007 |

OTHER PUBLICATIONS

International Search Report—PCT/KR2009/007083 dated Jul. 26, 2010.

* cited by examiner

*Primary Examiner* — Gordon J Stock, Jr.
(74) *Attorney, Agent, or Firm* — Cantor Colburn LLP

(57) ABSTRACT

Provided is a multi-channel surface plasmon resonance sensor using beam profile ellipsometry; and, more particularly, to a high sensitive measuring technology, which is coupled with a vertical illumination type focused-beam ellipsometer using a multi-incident angle measurement method, and a surface plasmon resonance (SPR) sensing part deposited with a metal thin film. The multi-channel surface plasmon resonance sensor includes a vertical illumination type focused-beam ellipsometer in which light is polarized; a surface plasmon resonance (SPR) sensing part which is provided at the objective lens part of the focused-beam ellipsometer; and a multi-channel flow unit which supplies a buffer solution containing a bio material binding to or dissociation from a metal thin film generating surface plasmon.

5 Claims, 5 Drawing Sheets

MULTI-CHANNEL SURFACE PLASMON RESONANCE SENSOR USING BEAM PROFILE ELLIPSOMETRY

The present invention claims priority of Korean Patent Application No. 10-2008-0120134, filed on Nov. 28, 2008, which is incorporated herein by reference.

TECHNICAL FIELD

The present invention relates to a multi-channel surface plasmon resonance sensor using beam profile ellipsometry; and, more particularly, to a high sensitive measuring technology, which is coupled with a vertical illumination type focused-beam ellipsometer using a multi-incident angle measurement method, and a surface plasmon resonance (SPR) sensing part deposited with a metal thin film (or a high numerical aperture objective lens, a refractive index matching material, a glass substrate deposited with a metal thin film) so as to allow real-time SPR measurement with respect to a sample having a micro channel.

The present invention relates to a multi-channel surface plasmon resonance sensor using beam profile ellipsometry; and, more particularly, to a high sensitive measuring technology, which is coupled with a polarizer, an ellipsometer using an analyzer, and a high numerical aperture objective lens part deposited with a metal thin film (or a high numerical aperture objective lens, a refractive index matching material, a glass substrate deposited with a metal thin film) so as to allow real-time SPR measurement with respect to a sample having multi-channels.

BACKGROUND ART

In general, an ellipsometer is a measuring device which obtains optical properties of a sample by measuring a change in a polarizing state after light having a specific polarizing state is incident to a surface of the sample and reflected from it, and then analyzing the measured values. Particularly, in the semiconductor industrial field using various manufacturing methods of nano thin film, the ellipsometer is widely used as a non-destructive and non-contacted real-time measuring technology for estimating physical properties of the manufactured nano thin films. Typically, the ellipsometer obtains data about an angle change relevant to the amplitude of light reflected from the sample.

A conventional ellipsometer can be applied to a semiconductor sample, but can not be applied to a biomaterial like protein. Preferably, a surface plasmon resonance (SPR) sensor is used for measure the properties of the biomaterial.

Electrons on a surface of a metal are collectively vibrated by normal directional vibration with respect to the surface of the metal, and this motion is called 'surface plasmon wave'. The vibration of quantized electrons is the surface plasmon. In order to quantitatively analyze a material using a phenomenon that the surface plasmon is excited by light waves, there have been various SPR sensors.

The resonance phenomenon of the surface plasmon is applied to a polarizer, or mainly applied to a bio-sensor, i.e., an opto-chemical sensor by using sensitivity with respect to polarizing characteristic of light.

A sensor using a resonance absorbing effect of the surface plasmon, i.e., a surface plasmon sensor is used for measuring a change in a concentration, a thickness or a refractive index of a dielectric substance contacted with the surface of the metal, and also may be used as a bio-sensor for measuring a change in a concentration of a sample like a bio material in real time without labeling.

FIG. 1 shows an example of a conventional SPR sensor.

As shown in the drawing, the SPR sensor includes a light source 110, a polarizer 120 for polarizing light emitted from the light source 110, a prism 130 in which the polarized light is incident and then reflected, a glass substrate 140 which is provided on one surface of the prism 130 and to which the polarized light passing through the prism 130 is incident, a metal thin film 150 which is coated on the glass substrate 140 with a nano-meter thickness so that the polarized light passing through the glass substrate 140 is reflected by surface plasmon resonance, and a light receiving part 160 for detecting the light reflected by the metal thin film and passed through the glass substrate 140 and the prism 130. Meanwhile, the metal thin film is contacted with a sample 170. If the concentration, thickness or refractive index of the sample 170 is changed between the metal thin film 150 and the sample 170, conditions of the SPR are correspondingly changed. Thus, the quantity of light reflected to the light receiving part 160 is changed, and the change in the concentration of the sample 170 contacted with the metal thin film 150 is measured by using this phenomenon.

The SPR measurement is performed under optimal SPR conditions. However, since the conventional SPR sensor uses only a reflectance ratio, the optical SPR conditions with respect to the phase change is not sensitively changed, and thus the measuring precision is deteriorated.

Especially, when a low molecular material used as a new drug candidate is conjugated to target protein, it is required to provide the extremely sensitive measuring precision. However, in the conventional SPR sensor, it is difficult to perform the high sensitive measurement.

In addition, since the conventional SPR measurement is restrictively performed at only a local region, it is impossible to measure a sample having multi-channels.

DISCLOSURE OF INVENTION

Solution to Problem

An embodiment of the present invention is directed to providing a multi-channel surface plasmon resonance sensor using beam profile ellipsometry, which can be applied to a sample having multi-channels, and also provides a highly sensitive measuring precision by allowing the optimal SPR conditions with respect to the phase change to be sensitively changed.

To achieve the object of the present invention, the present invention provides a multi-channel surface plasmon resonance sensor using beam profile ellipsometry, including a vertical illumination type focused-beam ellipsometer in which light is polarized, a part of the polarized light is focused to a metal thin film 42 having multi-channels by using an objective lens part, and then the polarized light reflected from the metal thin film 42 is detected so as to measure a ellipsometric phase change; a surface plasmon resonance (SPR) sensing part 40 which is provided at the objective lens part of the focused-beam ellipsometer so as to generate SPR according to an angle change of the polarized light; and a multi-channel flow unit 1 which supplies a buffer solution containing a bio material binding to or dissociaion from the metal thin film 42 generating surface plasmon, wherein the SPR and the ellipsometric phase change by change in an angle and a wavelength are simultaneously detected.

Preferably, the vertical illumination type focused-beam ellipsometer includes a light source 10; a polarizer 20 for polarizing light emitted from the light source 10; a beam splitter 30 for splitting the light polarized from the polarizer 20; an objective lens 41, 43 for focusing a part of the polarized light split from the beam splitter 30 to a metal thin film 42 having the multi-channels; an analyzing means 50 for polarizing the light linearly reflected from the metal thin film 42 and passed through the beam splitter 30, and detecting the polarized light; an imaging module 60 for imaging the light detected by the analyzing means 50; an optical detector 70 for detecting amplitude and phase of the light imaged by the imaging module 60; and a processing device 80 for processing the ellipsometric phase change detected by the optical detector 70.

Preferably, the light source 10 is one of a light source for emitting a short wavelength or a wavelength band of an ultraviolet ray, visible ray or an infrared ray, and a wavelength variable light source of a wavelength variable laser or diode.

Preferably, the analyzing means 50 is one of an analyzer, a single polarizing-beam splitter, a beam splitter and a polarizer.

Preferably, the SPR sensing part 40 includes a first lens 41 which is a cylindrical shape converging lens for linearly focusing a part of the polarized light; and a second lens 43 which is a single cylindrical lens or a group of cylindrical lenses that the metal thin film 42 is deposited on a final surface of the lens so as to obtain a high numerical aperture together with the first lens 41.

Preferably, the SPR sensing part 40 includes a third lens 44 which is formed into a single cylindrical lens or a group of cylindrical lenses so as to linearly focus a part of the polarized light; a glass substrate 45 which is provided at a lower side of the third lens 44 and of which a lower side is deposited with the metal thin film 42; and a refractive index matching material 46 which is interposed between the third lens 44 and the glass substrate 45 so as to match a refractive index of the third lens 44 and a refractive index of the glass substrate 45 with each other.

Preferably, the multi-channel surface plasmon resonance sensor further includes a means for rotating the polarizer 20 or the analyzer 50 in a vertical direction to a running direction of the light or polarization-modulating the light, so that the linear light detected by the analyzer 50 can be detected at each incident angle by the optical detector 70.

Preferably, the multi-channel surface plasmon resonance sensor further includes a compensator 90 which is disposed between the beam splitter 30 and the SPR sensing part 40 or between the beam splitter 30 and the optical detector 70 so as to compensate the light split from the beam splitter 30.

Preferably, the multi-channel surface plasmon resonance sensor further includes a rotating means for rotating the compensator 90 in a vertical direction to a running direction of the light, so that the light compensated by the compensator 90 can be detected at each incident angle by analyzer 50 so as to provide multi-channel information according to a change in position.

Preferably, the multi-channel surface plasmon resonance sensor further includes a collimator 100 which is disposed between the light source 10 and the polarizer 20 so as to convert the light emitted from the light source 10 into parallel light and then transmit the parallel light to the polarizer 20.

Preferably, the SPR sensing part 40 includes a first lens 41 which is a cylindrical shape converging lens for linearly focusing a part of the polarized light; a second lens 43 which is a single cylindrical lens or a group of cylindrical lenses so as to obtain a high numerical aperture together with the first lens 41; a glass substrate 45 which is provided at a lower side of the second lens 43 and of which a lower side is deposited with the metal thin film 42; and a refractive index matching material 46 which is interposed between the second lens 43 and the glass substrate 45 so as to match a refractive index of the second lens 43 and a refractive index of the glass substrate 45 with each other.

Preferably, the converging lens 41 is formed into one of a biconvex shape, a planoconvex shape and a meniscus shape.

Advantageous Effects of Invention

According to the present invention, it is possible to facilely measure the sample having the multi-channel, and also it is possible to measure a conjugation property and a conjugation dynamic property of the bio material in real time by simultaneously measuring the amplitude and the phase of the light and thus simultaneously measuring the ellipsometric phase change and the SPR measurement caused by the angle change and the phase change. Further, since it is possible to perform the measurement in the optimal SPR condition in which the phase change is sensitive, it is possible to perform the higher sensitive measurement than the conventional SPR measurement using only the reflexibility.

While the present invention has been described with respect to the specific embodiments, it will be apparent to those skilled in the art that various changes and modifications may be made without departing from the spirit and scope of the invention as defined in the following claims.

DETAILED DESCRIPTION OF MAIN ELEMENTS

Figure 1:
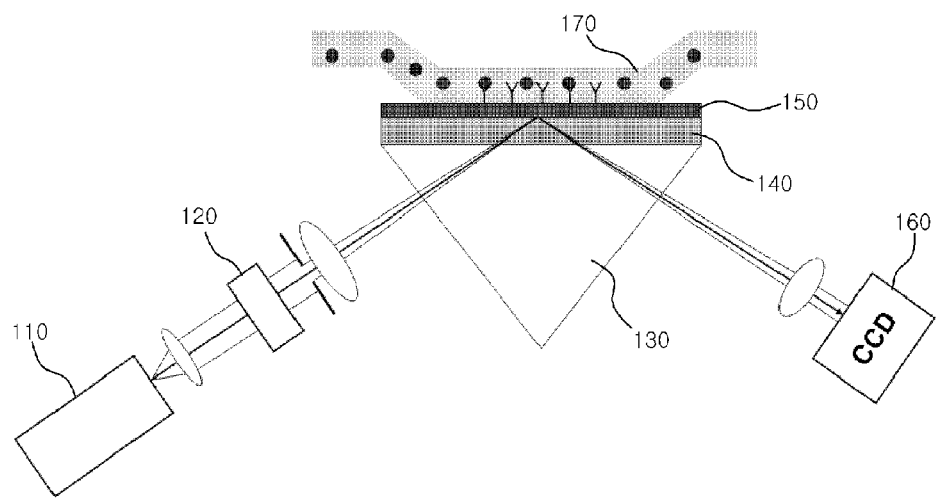
FIG. 1 is a schematic view of a conventional surface plasmon resonance (SPR) sensor.

1: multi-channel flow unit
1a: bio thin film
1b: buffer solution
10: light source
20: polarizer
30: beam splitter
40: objective lens
41: first lens
42: metal thin film
43: second lens
44: third lens
45: glass substrate
46: refractive index matching material
50: analyzer
60: imaging module
70: optical detector
80: processing device
90: compensator
100: collimator Mode for the Invention The present invention relates to a multi-channel surface plasmon resonance sensor using beam profile ellipsometry;

and, more particularly, to a high sensitive measuring technology, which is coupled with a vertical illumination type focused-beam ellipsometer using a multi-incident angle measurement method, and a surface plasmon resonance (SPR) sensing part deposited with a metal thin film (or a high numerical aperture objective lens, a refractive index matching material, a glass substrate deposited with a metal thin film) so as to allow real-time SPR measurement with respect to a sample having a micro channel. The ellipsometry can simultaneously measure amplitude and phase of light reflected from a surface of a sample. Particularly, if the beam profile ellipsometry is performed under optimal SPR conditions in which a phase change is sensitive, it is possible to perform the measurement having higher sensitivity than a conventional SPR measuring method only using a reflectance ratio. A conventional focused beam ellipsometer is used in a semiconductor sample and has no connection with a SPR measurement of the present invention.

Hereinafter, the multi-channel surface plasmon resonance sensor using beam profile ellipsometry will be described fully with reference to the drawings.

Figure 2:
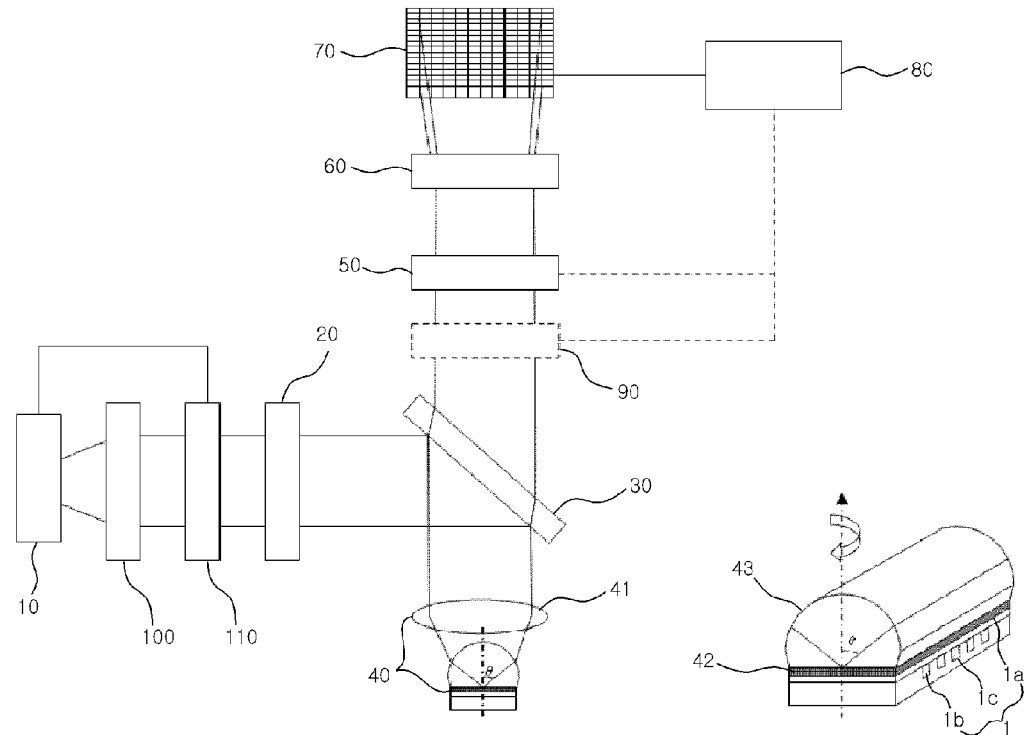
FIG. 2 is a view showing a structure of a multi-channel SPR sensor using beam profile ellipsometry in accordance with the present invention.
Figure 3:
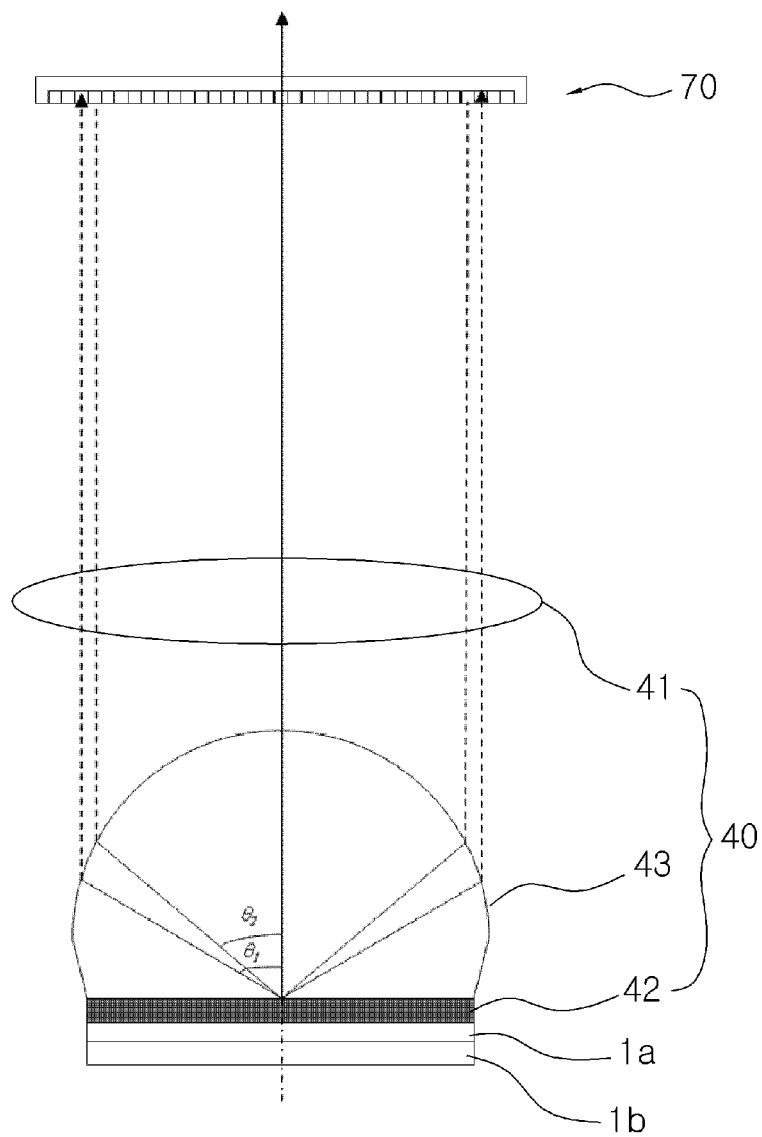
FIG. 3 is a view showing an optical detection path.
Figure 4:
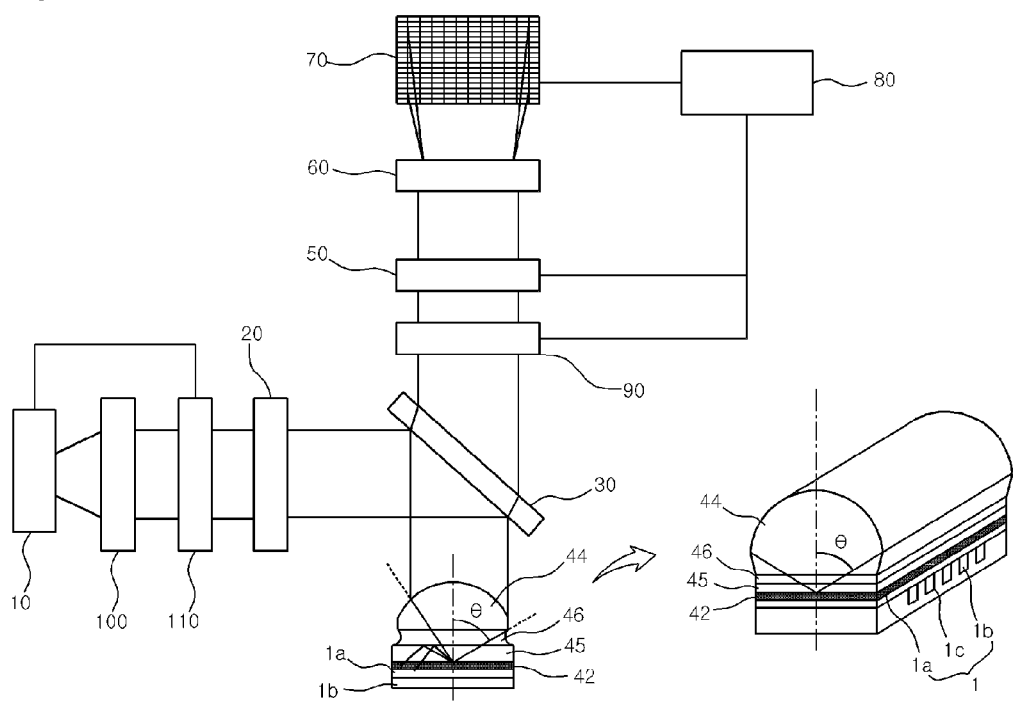
FIG. 4 is a view showing a structure of other type multi-channel SPR sensor using beam profile ellipsometry in accordance with the present invention.

FIG. 2 is a view showing a structure of a multi-channel SPR sensor using beam profile ellipsometry in accordance with the present invention, FIG. 3 is a view showing an optical detection path, and FIG. 4 is a view showing a structure of other type multi-channel SPR sensor using beam profile ellipsometry in accordance with the present invention.

As shown in the drawings, a multi-channel SPR sensor using beam profile ellipsometry according to the present invention includes a vertical illumination type focused-beam ellipsometer having a light source 10, a first polarizer 20 for polarizing light emitted from the light source 10, a beam splitter 30 for splitting the polarized light, an objective lens 41, 43 for focusing a part of the split polarized light to a metal thin film 42, an analyzer 50 for polarizing the light reflected from the metal thin film 42 and detecting the polarized light, an imaging module 60 for imaging the light detected by the analyzer 50, an optical detector 70 for detecting amplitude and phase of the polarized light and simultaneously detecting multi-channel SPR and ellipsometric phase change caused by the angle change and the phase change, and a processing device 80 for processing the detected SPR and the ellipsometric phase change; a SPR sensing part 40 including the metal thin film 42 which is coupled with the objective lens 43 of the focused-beam ellipsometer so as to generate the SPR caused by the angle change; and a multi-channel flow unit 1 which supplies a buffer solution including a bio material binding to or dissociation from the metal thin film 42 generating surface plasmon.

The light source 10 may emit a short wavelength or a wavelength band of an ultraviolet ray, visible ray or an infrared ray. Further, the light source 10 may be a wavelength variable light source of a wavelength variable laser or diode and the like so as to perform the measurement at a desired wavelength proper to the optimal sensitivity condition of the SPR according to a thickness difference of the metal thin film 42.

When a white light source is used as the light source 10, a monochromator 110 is further provided between the light source 10 and the polarizer 20, or the monochromator (not shown) is provided at the analyzer 50.

The polarizer 20 functions to polarize the light emitted from the light source 10.

The beam splitter 30 splits the light polarized from the polarizer 20 and transmits a part of the split light to the SPR sensing part 40.

The SPR sensing part 40 focuses to the metal thin film 42 a part of the polarized light split from the beam splitter 30. At this time, the multi-channel flow unit 1 for supplying the buffer solution 1b including the bio material includes a bio thin film 1a and a micro channel 1c which is formed at a lower side of the bio thin film 1a so as to be filled with the buffer solution 1b.

For example, as shown in FIG. 2, the SPR sensing part 40 includes two lenses, i.e., a first lens 41 which is a cylindrical shape converging lens for linearly focusing a part of the polarized light split from the beam splitter 30, and a second lens 43 which is a single cylindrical lens or a group of cylindrical lenses that the metal thin film 42 is deposited on a surface of the lens so as to obtain a high numerical aperture together with the first lens 41.

The converging lens may be formed into a biconvex shape, a planoconvex shape or a meniscus shape.

After a part of the polarized light split from the beam splitter 30 is focused by the first lens 41, the polarized light focused by the first lens 41 is focused to the metal thin film 42 by the second lens 43. At this time, the second lens 43 is formed into the single cylindrical lens or the group of cylindrical lenses so as to obtain the high numerical aperture together with the first lens 41, and the metal thin film 42 is deposited on a lower flat surface of the second lens 43. The metal thin film 42 is formed of a metal material such as Au and Ag.

Furthermore, the SPR sensing part 40 may include the second lens 43 which functions to focus a part of the polarized light split from the beam splitter 30 and which is formed into the single cylindrical lens or the group of cylindrical lenses so as to obtain the high numerical aperture together with the first lens 41, the glass substrate (not shown) which is provided at a lower side of the second lens 43 so as to be deposited with the metal thin film 42, and a refractive index matching material (not shown) which is interposed between the second lens 43 and the glass substrate (not shown) so as to match a refractive index of the second lens 43 and a refractive index of the glass substrate (not shown) with each other.

As another example shown in FIG. 4, the SPR sensing part 40 may include an integral lens, the glass substrate and the refractive index matching material. The SPR sensing part 40 includes a third lens 44 which functions to focus a part of the polarized light split from the beam splitter 30 and which is formed into the single cylindrical lens or the group of cylindrical lenses, the glass substrate 45 which is provided at a lower side of the third lens 44 so as to be deposited with the metal thin film 42, and a refractive index matching material 46 which is interposed between the third lens 44 and the glass substrate 45 so as to match a refractive index of the third lens 44 and a refractive index of the glass substrate 45 with each other.

Herein, refractive index matching oil and thin film are used as the refractive index matching material 46. Preferably, the glass substrate deposited with the metal thin film 42 has a structure that can be easily replaced with new one. The refractive index matching material 46 functions to increase a maximum incident angle of light through the third lens 44. In case that the refractive index matching material 46 is not used, since total reflection is occurred in the air, it is impossible to perform the SPR measurement.

If a part of the polarized light split from the beam splitter 30 is linearly focused by the third lens 44, the focused light is incident to the glass substrate 45 by the refractive index matching material 46, and the incident polarized light is focused to the metal thin film 42 which is deposited at the lower side of the glass substrate 45 and contacted with the multi-channel flow unit 1. If a concentration, a thickness or a refractive index of the bio thin film 1a is changed in the multi-channel flow unit 1, the SPR condition is changed, and the light is reflected and emitted to the glass substrate 45. And the emitted light is passed through the refractive index matching material 46 and then directed to the third lens 44. The light directed to the third lens 44 is passed through the beam splitter 30 and then detected by the analyzer 50.

The lens used in the present invention includes a high numerical aperture objective lens, a SIL lens and the like.

Herein, the maximal incident angle of the light that is incident to the lens is determined by a numerical aperture NA of the lens and a refractive index n of a medium.

$$\theta_{max} = \sin^{-1}\left(\frac{NA}{n}\right)$$

In the present invention, it is possible to simultaneously measure the SPR and the ellipsometric phase change according to the change in angle and wavelength by using a vertical illumination type focused-beam ellipsometer using a multi-incident angle measurement method, and the SPR sensing part 40 deposited with a metal thin film (or a high numerical aperture objective lens, a refractive index matching material, a glass substrate deposited with a metal thin film), and also it is possible to measure a conjugation property and a conjugation dynamic property of the bio material in real time.

The analyzer 50 functions to polarize the light reflected from the metal thin film 42 and passed through the objective lens and the beam splitter 30 and then detect the polarized light.

The optical detector 70 functions to detect the amplitude and phase of the polarized light detected by the analyzer 50. Herein, as shown in FIG. 3, the optical detector 70 detects the light which is reflected at various angles. One axis of a second dimensional optical detector detects a signal according to an angle, and the other axis thereof detects a signal of other channel according to a position in the same way. Therefore, the present invention can detect multi-channel signals.

The processing device 80 processes the SPR and the ellipsometric phase change detected by the optical detector 70.

In the processing method, a ellipsometric coefficient $\Psi$, $\Delta$ is calculated from the principle of the ellipsometry having a polarizer-sample-analyzer (PSA) or polarizer-sample-compensator-analyzer (PSCA) type structure in each unit device (the unit pixel in case of CCD).

As shown in FIG. 3, it is possible to obtain information of the angle from one axis of a second dimensional unit device and the channel position from other axis thereof.

The ellipsometric coefficient $\Psi$ relevant to the amplitude is used for calculating the angle change in the SPR measurement and designates a minimum value in the optimal resonance condition. A movement amount of the angle is corresponding to a movement amount of the SPR angle, and a change in a value of $\Psi$ can be also used for calculating the resonance angle. The ellipsometric coefficient $\Psi$ relevant to the amplitude provides information like the change in the SPR angle, and the $\Delta$ which designates the phase change can be used in performing precise SPR measurement. The phase change $\Delta$ is sensitively changed under the optimal SPR condition. In other words, the phase change is maximal in the optimal SPR condition. Therefore, if the change in a phase value in the optimal SPR condition is measured, it can be used in adsorption dynamic property of various bio materials (e.g., adsorption dynamic property of a low molecular material used as a new drug candidate, etc.), which requires a precise measurement, and it can be also used in calculation and quantifying of the SPR angle by simultaneously using the amplitude and the phase. Particularly, when a low molecular material used as a new drug candidate is conjugated to target protein, it is required to provide the extremely sensitive measuring precision. In this case, the phase measurement can show better characteristics than the conventional measurement of reflexibility.

In the ellipsometric equation, a complex reflection coefficient ratio $\rho$ is a reflection coefficient ratio ($r_s$, $r_p$) with respect to p-wave and s-wave, and can be expressed as follows.

$$\rho = \frac{r_p}{r_s} = \tan\Psi e^{i\Delta}$$

In addition, it is preferable to further provide a collimator 100 which is disposed between the light source 10 and the polarizer 20 so as to convert the light emitted from the light source 10 into parallel light and then transmit the parallel light to the polarizer 20.

Further, it is preferable to further provide a compensator 90 which is disposed between the beam splitter 30 and the SPR sensing part 40 or between the beam splitter 30 and the optical detector 70 so as to compensate the light split from the beam splitter 30.

As shown in FIGS. 2 and 4, there may be further provided a means (not shown) for rotating the polarizer 20 or the analyzer 50 in a vertical direction to a running direction of the light or polarization-modulating the light, so that the light detected by the analyzer 50 can be detected at each incident angle by the optical detector 70. In the same way, there may be further provided a rotating means (not shown) for rotating the compensator 90 in the vertical direction to the running direction of the light, so that the light compensated by the compensator 90 can be detected at each incident angle by the analyzer 50.

The optimal SPR condition easily changes the wavelength and the angle of the light according to a thickness of the metal thin film 42 deposited on the glass substrate. Therefore, in case that an ellipsometric structure, in which one of the polarizer, the analyzer and the compensator of the SPR sensing part 40 is rotated, is used, it is possible to perform the measurement in the optimal SPR condition without deterioration of the sensitivity, which may be occurred by the error of a thickness or physical property when manufacturing the metal thin film 42.

In a method of measuring the angle according the change in the wavelength using the ellipsometric in which one of the analyzer 50 and the compensator 90 of the SPR sensing part 40 is rotated, it is possible to perform the measurement in the optimal SPR condition that can be changed according to a process condition. The phase measurement using the ellipsometry is most sensitively changed in the optimal SPR condition. However, since the refractive index and the thickness of the metal thin film 42 that is a core part of the SPR sensor may be easily changed according to a manufacturing process, it is possible to easily obtain the optimal SPR condition within a measuring angle and a wavelength range of the used light source and thus it is possible to simultaneously use the advantage of the SPR and the ellipsometry.

A reference numeral 110 which is not descried is a monochromator.

Embodiment (measurement of change in SPR angle according to wavelength)

Figure 5:
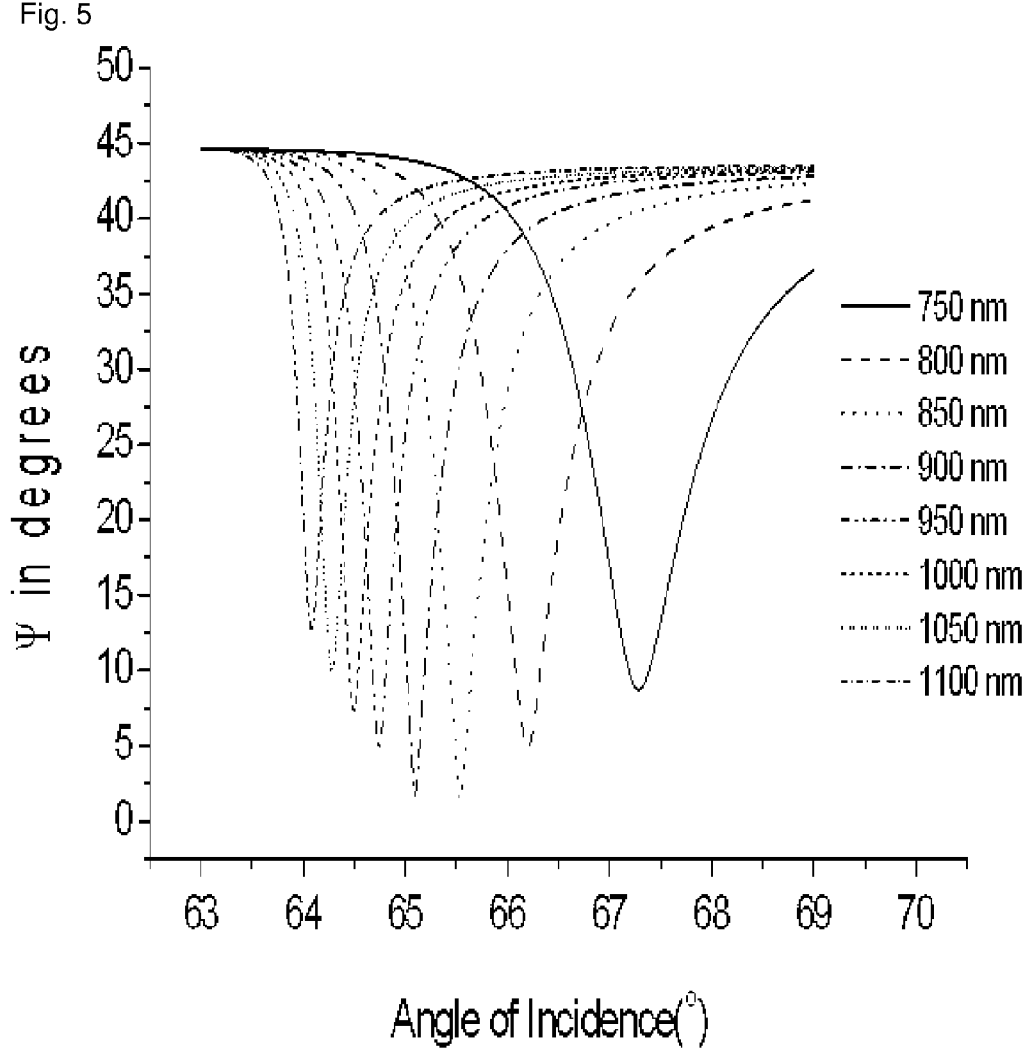
FIG. 5 is a graph showing a change in SPR angle according to a wavelength when using BK7 lens.
Figure 6:
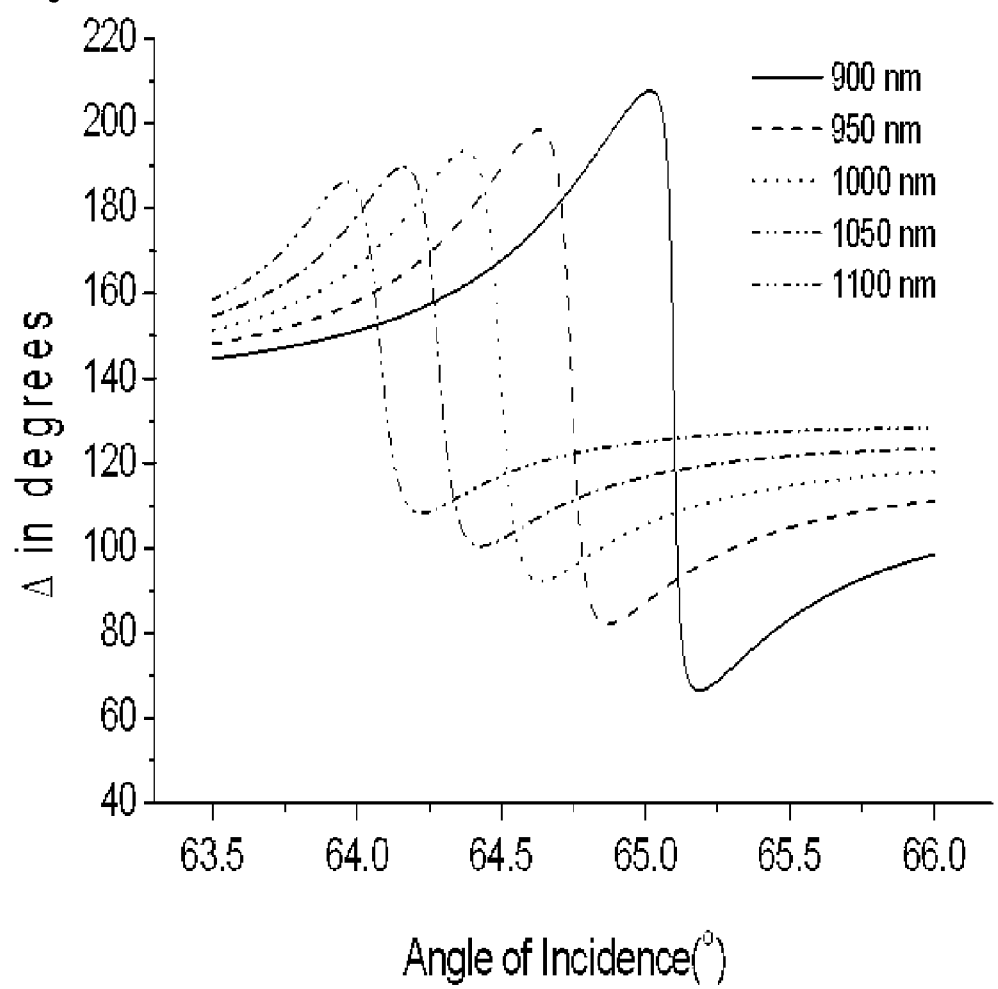
FIG. 6 is a graph showing an inclination of a phase change according to a wavelength and an angle.

The change in the SPR angle according to the wavelength was measured and then shown in FIGS. 5 and 6, wherein the wavelength was 750 to 1100 nm, the lens was formed of BK7, the metal thin film was formed of Au, a thickness of the metal thin film was 45 nm, and a refractive index of the buffer solution was 1,333.

FIG. 5 shows that the SPR angle is changed according to a wavelength, and FIG. 6 shows that an inclination of the phase change is changed according to a wavelength and also it is possible to select the angle and the wavelength in which the inclination of the phase change is maximal.

The invention claimed is:

1. A multi-channel surface plasmon resonance sensor using beam profile ellipsometry, comprising:
    a vertical illumination focused-beam ellipsometer in which light is polarized, a part of the polarized light is focused to a metal thin film having multi-channels by using an objective lens part, and then the polarized light reflected from the metal thin film is detected so as to measure an ellipsometric phase change;
    a surface plasmon resonance (SPR) sensing part which is provided at the objective lens part of the focused-beam ellipsometer so as to generate surface plasmon resonance (SPR) according to an angle change of the polarized light; and
    a multi-channel flow unit which supplies a buffer solution containing a bio material binding to or dissociation from the metal thin film generating surface plasmon,
    wherein the SPR and the ellipsometric phase change by change in an angle and a wavelength are simultaneously detected,
    wherein the SPR sensing part comprises:
    a first lens which is a cylindrical shape converging lens for linearly focusing a part of the polarized light; and
    a second lens which is a single cylindrical lens or a group of cylindrical lenses that the metal thin film is deposited on a final surface of the second lens.

2. The multi-channel surface plasmon resonance sensor of claim 1, wherein the converging lens is formed into one of a biconvex cylindrical lens, a planoconvex cylindrical lens and a meniscus cylindrical lens.

3. The multi-channel surface plasmon resonance sensor of claim 1, wherein the SPR sensing part comprises:
    a glass substrate which is provided at a lower side of the second lens and of which a lower side is deposited with the metal thin film; and
    a refractive index matching material which is interposed between the second lens and the glass substrate so as to match a refractive index of the second lens and a refractive index of the glass substrate with each other.

4. The multi-channel surface plasmon resonance sensor of claim 3, wherein the converging lens is formed into one of a biconvex cylindrical lens, a planoconvex cylindrical lens and a meniscus cylindrical lens.

5. A multi-channel surface plasmon resonance sensor using beam profile ellipsometry, comprising:
    a vertical illumination focused-beam ellipsometer in which light is polarized, a part of the polarized light is focused to a metal thin film having multi-channels by using an objective lens part, and then the polarized light reflected from the metal thin film is detected so as to measure an ellipsometric phase change;
    a surface plasmon resonance (SPR) sensing part which is provided at the objective lens part of the focused-beam ellipsometer so as to generate surface plasmon resonance (SPR) according to an angle change of the polarized light; and
    a multi-channel flow unit which supplies a buffer solution containing a bio material binding to or dissociation from the metal thin film generating surface plasmon,
    wherein the SPR and the ellipsometric phase change by change in an angle and a wavelength are simultaneously detected,
    wherein the SPR sensing part comprises:
    a lens which is formed into a single cylindrical lens or a group of cylindrical lenses so as to linearly focus a part of the polarized light;
    a glass substrate which is provided at a lower side of the lens and of which a lower side is deposited with the metal thin film; and
    a refractive index matching material which is interposed between the lens and the glass substrate so as to match a refractive index of the third lens and a refractive index of the glass substrate with each other.

* * * * *